(12) United States Patent
Hastings et al.

(10) Patent No.: US 11,896,287 B2
(45) Date of Patent: *Feb. 13, 2024

(54) VAPOR ABLATION SYSTEMS AND METHODS

(71) Applicant: Boston Scientific Scimed, Inc., Maple Grove, MN (US)

(72) Inventors: Roger Noel Hastings, Naples, FL (US); Mark Schrom, Forest Lake, MN (US); Steven Carlson, St. Paul, MN (US); Michael Hoey, Shoreview, MN (US); Timothy D. Byland, Plymouth, MN (US); Karliam C. Woo, Maple Grove, MN (US); Brian A. Bachmeier, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 129 days.

This patent is subject to a terminal disclaimer.

(21) Appl. No.: 17/646,129

(22) Filed: Dec. 27, 2021

(65) Prior Publication Data

US 2022/0117648 A1    Apr. 21, 2022

Related U.S. Application Data

(63) Continuation of application No. 15/781,721, filed as application No. PCT/US2016/067558 on Dec. 19, 2016, now Pat. No. 11,246,642.

(60) Provisional application No. 62/357,742, filed on Jul. 1, 2016, provisional application No. 62/269,776, filed on Dec. 18, 2015.

(51) Int. Cl.
*A61B 18/14* (2006.01)
*A61B 18/04* (2006.01)
(Continued)

(52) U.S. Cl.
CPC .............. *A61B 18/14* (2013.01); *A61B 18/04* (2013.01); *A61B 18/042* (2013.01); *F22B 1/28* (2013.01);
(Continued)

(58) Field of Classification Search
CPC ....... A61B 18/04; A61B 18/042; A61B 18/14; A61B 2018/00547; A61B 2018/00577;
(Continued)

(56) References Cited

U.S. PATENT DOCUMENTS

| | | | |
|---|---|---|---|
| 5,531,763 A | 7/1996 | Mastri et al. | |
| 2003/0199903 A1 | 10/2003 | Boecker et al. | |

(Continued)

FOREIGN PATENT DOCUMENTS

| | | |
|---|---|---|
| JP | 4703243 B2 | 6/2011 |
| JP | 2019-505266 A | 2/2019 |

(Continued)

*Primary Examiner* — Tigist S Demie
(74) *Attorney, Agent, or Firm* — Bookoff McAndrews, PLLC

(57) ABSTRACT

A vapor delivery needle is provided that may include any of a number of features. One feature of the energy delivery probe is that it can apply condensable vapor energy to tissue, such as a prostrate, to shrink, damage, denaturate the prostate. In some embodiments, the vapor delivery needle can be advanced a predetermined distance into the prostate with a solenoid actuation mechanism. Methods associated with use of the energy delivery probe are also covered.

17 Claims, 14 Drawing Sheets

(51) Int. Cl.
*H01F 7/13* (2006.01)
*H01F 7/16* (2006.01)
*F22B 1/28* (2006.01)
*A61B 18/00* (2006.01)

(52) U.S. Cl.
CPC ............. *H01F 7/13* (2013.01); *H01F 7/1615* (2013.01); *A61B 2018/00547* (2013.01); *A61B 2018/00577* (2013.01); *A61B 2018/00827* (2013.01); *A61B 2018/048* (2013.01); *A61B 2018/1475* (2013.01); *H01F 2007/1692* (2013.01)

(58) Field of Classification Search
CPC .... A61B 2018/00827; A61B 2018/048; A61B 2018/1475; F22B 1/28; H01F 2007/1692; H01F 7/13; H01F 7/1615
See application file for complete search history.

(56) References Cited

U.S. PATENT DOCUMENTS

| | | |
|---|---|---|
| 2008/0214956 A1* | 9/2008 | Briggs ................ A61B 5/1519 600/583 |
| 2011/0238144 A1 | 9/2011 | Hoey et al. |
| 2011/0306950 A1 | 12/2011 | Cucin |
| 2014/0110508 A1 | 4/2014 | Dames et al. |
| 2014/0206985 A1 | 7/2014 | Kariv |
| 2014/0288543 A1 | 9/2014 | Hoey et al. |
| 2014/0354381 A1 | 12/2014 | Kohlhafer |
| 2015/0025515 A1* | 1/2015 | Hoey .................... F22B 1/281 219/630 |

FOREIGN PATENT DOCUMENTS

| | | |
|---|---|---|
| WO | 2010080467 A2 | 7/2010 |
| WO | 2014153082 A1 | 9/2014 |
| WO | 2015089190 A1 | 6/2015 |

* cited by examiner

VAPOR ABLATION SYSTEMS AND METHODS

CROSS REFERENCE TO RELATED APPLICATIONS

This application is a continuation of U.S. application Ser. No. 15/781,721, filed Jun. 6, 2018, which is a 35 U.S.C. § 371 National Stage entry of PCT Application No. PCT/US2016/067558, filed Dec. 19, 2016, which claims the benefit of priority of U.S. Provisional Application No. 62/269,776, filed Dec. 18, 2015, and U.S. Provisional Application No. 62/357,742, filed Jul. 1, 2016, all of which are herein incorporated by reference in their entireties.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD

The present invention relates to devices and related methods for treatment of benign prostatic hyperplasia using a minimally invasive approach.

BACKGROUND

Benign prostatic hyperplasia (BPH) is a common disorder in middle-aged and older men, with prevalence increasing with age. At age 50, more than one-half of men have symptomatic BPH, and by age 70, nearly 90% of men have microscopic evidence of an enlarged prostate. The severity of symptoms also increase with age with 27% of patients in the 60-70 age bracket having moderate-to-severe symptoms, and 37% of patients in their 70's suffering from moderate-to-severe symptoms.

The prostate early in life is the size and shape of a walnut and prior to the enlargement resulting from BPH, weighs about 20 grams. Prostate enlargement appears to be a normal process. With age, the prostate gradually increases in size to twice or more its normal size. The fibromuscular tissue of the outer prostatic capsule restricts expansion after the gland reaches a certain size. Because of such restriction on expansion, the intracapsular tissue will compress against and constrict the prostatic urethra, thus causing resistance to urine flow.

In the male urogenital anatomy, the prostate gland is located below the bladder and the bladder neck. The walls of the bladder can expand and contract to cause urine flow through the urethra, which extends from the bladder, through the prostate and penis. The portion of urethra that is surrounded by the prostate gland is referred to as the prostatic urethra. The prostate also surrounds the ejaculatory ducts which have an open termination in the prostatic urethra. During sexual arousal, sperm is transported from the testes by the ductus deferens to the prostate which provides fluids that combine with sperm to form semen during ejaculation. On each side of the prostate, the ductus deferens and seminal vesicles join to form a single tube called an ejaculatory duct. Thus, each ejaculatory duct carries the seminal vesicle secretions and sperm into the prostatic urethra.

The prostate glandular structure can be classified into three zones: the peripheral zone, transition zone, and central zone. Peripheral zone PZ comprises about 70% of the volume of a young man's prostate. This sub-capsular portion of the posterior aspect of the prostate gland surrounds the distal urethra and 70 to 80% of cancers originate in the peripheral zone tissue. The central zone CZ surrounds the ejaculatory ducts and contains about 20-25% of the prostate volume. The central zone is often the site of inflammatory processes. The transition zone TZ is the site in which benign prostatic hyperplasia develops, and contains about 5-10% of the volume of glandular elements in a normal prostate, but can constitute up to 80% of such volume in cases of BPH. The transition zone consists of two lateral prostate lobes and the periurethral gland region. There are natural barriers around the transition zone, i.e., the prostatic urethra, the anterior fibromuscular stroma, and a fibrous plane between the transition zone and peripheral zone. The anterior fibromuscular stroma or fibromuscular zone is predominantly fibromuscular tissue.

BPH is typically diagnosed when the patient seeks medical treatment complaining of bothersome urinary difficulties. The predominant symptoms of BPH are an increase in frequency and urgency of urination, and a significant decrease in the rate of flow during urination. BPH can also cause urinary retention in the bladder which in turn can lead to lower urinary tract infection (LUTI). In many cases, the LUTI then can ascend into the kidneys and cause chronic pyelonephritis, and can eventually lead to renal insufficiency. BPH also may lead to sexual dysfunction related to sleep disturbance or psychological anxiety caused by severe urinary difficulties. Thus, BPH can significantly alter the quality of life with aging of the male population.

BPH is the result of an imbalance between the continuous production and natural death (apoptosis) of the glandular cells of the prostate. The overproduction of such cells leads to increased prostate size, most significantly in the transition zone which traverses the prostatic urethra.

In early stage cases of BPH, pharmacological treatments can alleviate some of the symptoms. For example, alpha-blockers treat BPH by relaxing smooth muscle tissue found in the prostate and the bladder neck, which may allow urine to flow out of the bladder more easily. Such drugs can prove effective until the glandular elements cause overwhelming cell growth in the prostate.

More advanced stages of BPH, however, can only be treated by surgical or less-invasive thermal ablation device interventions. A number of methods have been developed using electrosurgical or mechanical extraction of tissue, and thermal ablation or cryoablation of intracapsular prostatic tissue. In many cases, such interventions provide only transient relief, and these treatments often cause significant peri-operative discomfort and morbidity.

In one thermal ablation method, RF energy is delivered to prostate tissue via an elongated RF needle being penetrated into a plurality of locations in a prostate lobe. The elongated RF needle is typically about 20 mm in length, together with an insulator that penetrates into the lobe. The resulting RF treatment thus ablates tissue away from the prostatic urethra and does not target tissue close to, and parallel to, the prostatic urethra. The application of RF energy typically extends for 1 to 3 minutes or longer which allows thermal diffusion of the RF energy to ablate tissue out to the capsule periphery. Such RF energy delivery methods may not create a durable effect, since smooth muscle tissue and alpha adrenergic receptors are not uniformly ablated around the prostatic urethra or within the transition zone. As a result, tissue in the prostate lobes can continue to grow and impinge on the urethra thus limiting long-term effectiveness of the treatment.

SUMMARY OF THE DISCLOSURE

A prostate treatment device is provided, comprising an introducer shaft sized and configured for transurethral access into a patient, a handle coupled to the introducer shaft, a vapor generator disposed in the handle and configured to generate a condensable vapor, a vapor delivery needle in communication with the vapor generator and slidably disposed within the introducer shaft, a magnet attached to the needle, and a solenoid actuator disposed around the magnet, the solenoid actuator comprising a push winding coupled to a source of RF current and a pull winding coupled to the source of RF current, the push winding being configured to apply a first magnetic field to the magnet, the pull winding being configured to apply a second magnetic field to the magnet, wherein the first and second magnetic fields move a distal tip of the vapor delivery needle between a retracted position inside the introducer shaft and an extended position at least partially outside of the introducer shaft.

In one embodiment, the first magnetic field shares a polarity with the magnet. In another embodiment, the second magnetic field has a polarity opposite to a polarity of the magnet.

In some embodiments, the combination of the first and second magnetic fields removes lateral movements of the magnet as the vapor delivery needle moves between the retracted position and the extended position.

In another embodiment, the combination of the first and second magnetic fields approximately doubles a force exerted by the push and pull windings to the magnet than would be exerted by a single winding.

In some embodiments, the solenoid actuator is configured to cause the distal tip of the vapor delivery needle to penetrate into prostate tissue when moving toward the extended position from the retracted position.

In one embodiment, the vapor delivery needle is sized and configured to extend into prostate tissue when the introducer shaft is positioned within a urethra of the patient.

In some embodiments, the handle is adapted for manual control of the solenoid actuator to move the vapor delivery needle between the retracted position and the extended position.

In another embodiment, the device comprises a vapor actuator configured to actuate a flow of condensable vapor through the vapor delivery needle.

In other embodiments, the magnet comprises a neodymium-iron-boron magnet.

In yet another embodiment, the device comprises a magnetic field sensor disposed near the solenoid actuator, the magnetic field sensor being configured to provide a voltage output proportional to a magnetic field produced by the magnet to determine a position of the vapor delivery needle. In some embodiments, vapor delivery is prevented if the voltage output of the magnetic field sensor indicates that the vapor delivery needle is not deployed.

In other embodiments, the device comprises a current sensor coupled to the push winding and to the pull winding, the current sensor being configured to detect back EMF when the push winding or pull winding is energized with a current source. In some embodiments, the back EMF manifests as a dip in current flowing through the current sensor.

In other embodiments, the back EMF indicates that the vapor delivery needle has properly deployed into the extended position.

A method of treating prostate tissue is provided, comprising inserting a shaft of a prostate therapy device transurethrally until a distal end of the shaft is proximate to the prostate tissue, actuating a solenoid assembly to advance a vapor delivery needle from the shaft into the prostate tissue, and delivering condensable vapor from the vapor delivery needle into the prostate tissue.

In some embodiments, the condensable vapor provides a thermal effect in the prostate tissue.

In one embodiment, a push winding of the solenoid assembly applies a first magnetic field to a magnet attached to the vapor delivery needle to advance the vapor delivery needle.

In another embodiment, a pull winding of the solenoid assembly applies a second magnetic field to the magnet to advance the vapor delivery needle.

An inductive vapor generator is provided, comprising a fluid source, an inner coil of tubing coupled to the fluid source, the inner coil comprising Inconel, an outer coil of conductive wire surrounding the inner coil of tubing, and an RF generator coupled to the outer coil and configured to apply RF current to the outer coil to inductively heat the inner coil to generate vapor.

In some embodiments, individual windings of the inner coil are soldered or welded together to ensure electrical contact between adjacent windings.

In one embodiment, the generator produces a calorie delivery efficiency greater than 75%.

In another embodiment, the inner coil comprises an inside diameter ranging from 0.75 mm to 0.95 mm.

A kit is provided, comprising a vapor delivery device having a handle, a shaft coupled to the handle, and a vapor delivery needle disposed partially within the shaft, and a hook feature disposed within the shaft, and a solenoid actuator configured to move a distal tip of the vapor delivery needle between a retracted position inside the shaft and an extended position at least partially outside of the shaft, retail packaging including a tray sized and configured to receive the vapor delivery device when the vapor delivery needle is extended distally beyond the shaft, the tray including an opening that is aligned with the hook feature when the vapor delivery device is inserted into the tray, and a pin inserted into the opening of the tray and configured to engage the hook feature of the vapor delivery device to lock the vapor delivery needle in place.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

DETAILED DESCRIPTION OF THE INVENTION

In general, one method for treating BPH comprises introducing a heated vapor interstitially into the interior of a prostate, wherein the vapor controllably ablates prostate tissue. This method can utilize vapor for applied thermal energy of between 50 calories and 300 calories per each individual vapor treatment (and assumes multiple treatments for each prostate lobe) in an office-based procedure. The method can cause localized ablation of prostate tissue, and more particularly the applied thermal energy from vapor can be localized to ablate tissue adjacent the urethra without damaging prostate tissue that is not adjacent the urethra.

The present disclosure is directed to the treatment of BPH, and more particularly for ablating transitional zone prostate tissue without ablating central or peripheral zone prostate tissue. In one embodiment, the present disclosure is directed to treating a prostate using convective heating in a region adjacent the prostatic urethra. The method of ablative treatment is configured to target smooth muscle tissue, alpha adrenergic receptors, sympathetic nerve structures and vasculature parallel to the prostatic urethra between the bladder neck region and the verumontanum region to a depth of less than 2 cm.

The system can include a vapor delivery mechanism that delivers vapor media, including water vapor. The system can utilize a vapor source configured to provide vapor having a temperature of at least 60-140° C. In another embodiment, the system further comprises a computer controller configured to deliver vapor for an interval ranging from 1 second to 30 seconds.

In some embodiments, the system further comprises a source of a pharmacologic agent or other chemical agent or compound for delivery with the vapor. These agents include, without limitation, an anesthetic, an antibiotic or a toxin such as Botox®, or a chemical agent that can treat cancerous tissue cells. The agent also can be a sealant, an adhesive, a glue, a superglue or the like.

In some embodiments, a prostate treatment device can be provided comprising an introducer shaft sized and configured for transurethral access into a patient, a vapor generator configured to generate a condensable vapor, a vapor delivery needle in communication with the vapor generator and slidably disposed within the introducer shaft, and a solenoid actuator configured generate a magnetic field to a vapor delivery needle to move the vapor delivery needle between a retracted position inside the introducer shaft and an extended position at least partially outside of the introducer shaft.

Figure 1A:
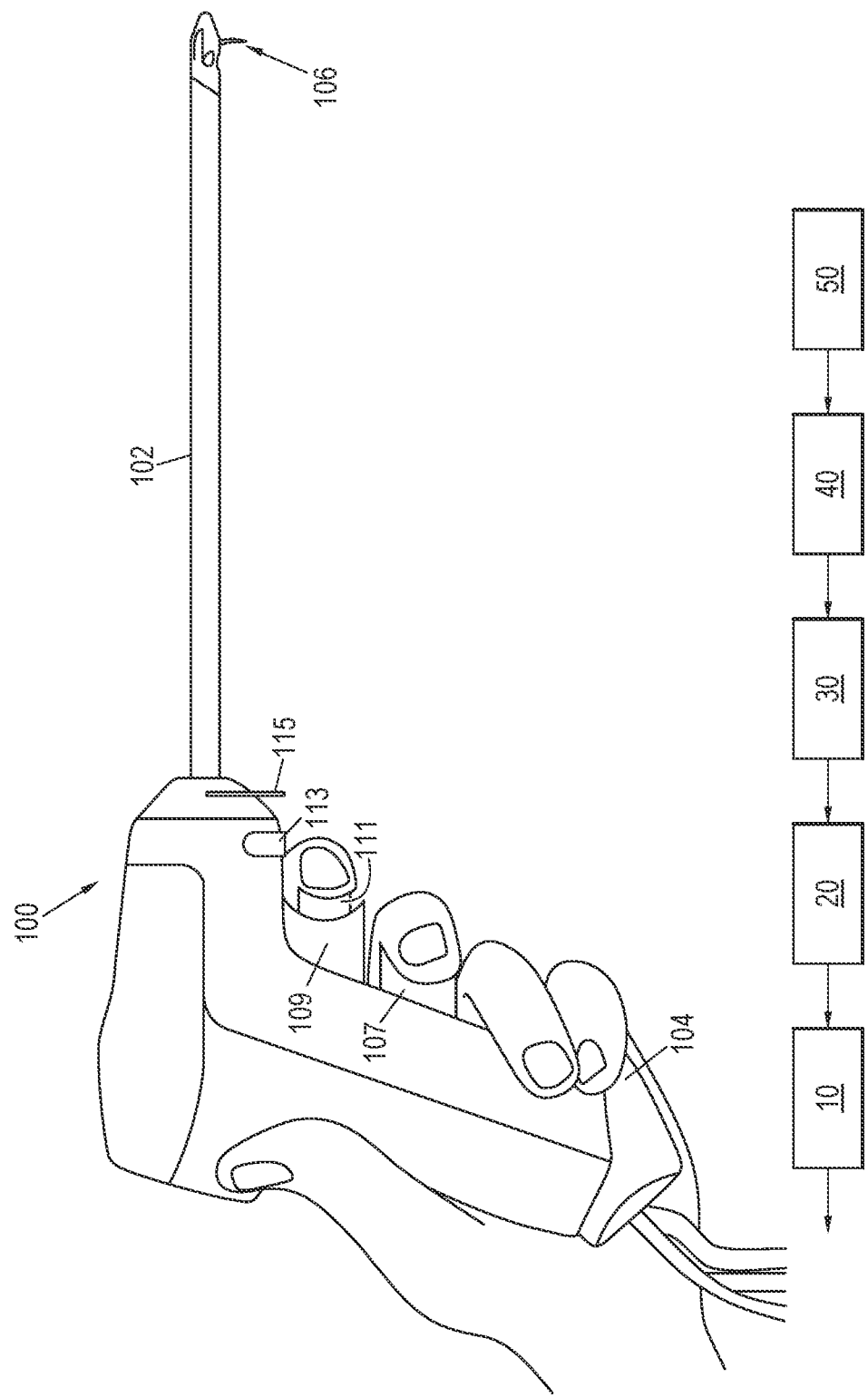
FIGS. 1A, 1B, 1C, 1D and 1E show one embodiment of a vapor delivery system.

FIG. 1A shows one embodiment of a vapor delivery system. Vapor delivery system 100 can have an elongate shaft 102 configured for insertion into the urethra of a patient and a handle portion 104 for gripping with a human hand. The vapor system 100 can include a vapor delivery needle 106 disposed in the shaft and configured to extend from a distal portion of the elongate shaft 102.

The handle can be an ergonomic swept back handle that allows the user to comfortably rotate the delivery device left and right to deliver vapor to the right and left lobes of the prostate. The vapor delivery needle can extend generally perpendicular to or transverse from the shaft, and can include one or more vapor delivery ports configured to deliver a flow of vapor media from the needle into prostate tissue.

The vapor delivery system 100 can further include one or more triggers, buttons, levers, or actuation mechanisms configured to actuate the various functions of the system. As shown in FIG. 1A, the system can include a RF therapy trigger 107, a needle advance trigger 109, a flush trigger 111, a needle retract button 113, and an emergency needle release ring 115. The needle advance trigger can be configured to extend/retract the vapor delivery needle, the RF therapy trigger can be configured to start/stop the flow of vapor, and the flush trigger can be configured to initiate a cooling and/or irrigation fluid such as saline.

In some embodiments, the triggers or actuation mechanisms can be manipulated in such a way as to control varying degrees or flow rates of vapor and/or irrigation. For example, a single press or depression of one of the triggers may provide a standard irrigation flush, while a rapid double press or depression of the trigger may provide a "turbo" irrigation flush in which the flow rate of irrigation is increased over the standard flush flow rate. This feature may be useful, for example, if the physician encounters a blockage, needs additional cooling, or has reduced vision in the urethra and/or prostate due to accumulation of blood or other bodily fluids.

The vapor delivery system 100 can be connected to a vapor source 10, an aspiration source 20, a fluid cooling or irrigation source 30, a light source 40, and/or an electronic controller 50 configured to control generation and delivery of vapor from the vapor source, through a lumen of the shaft, through the vapor delivery needle, and into tissue. In some embodiments, the electronic controller can be disposed on or in the vapor delivery system, and in other embodiments the electronic controller can be disposed separate from the system.

Figure 1B:
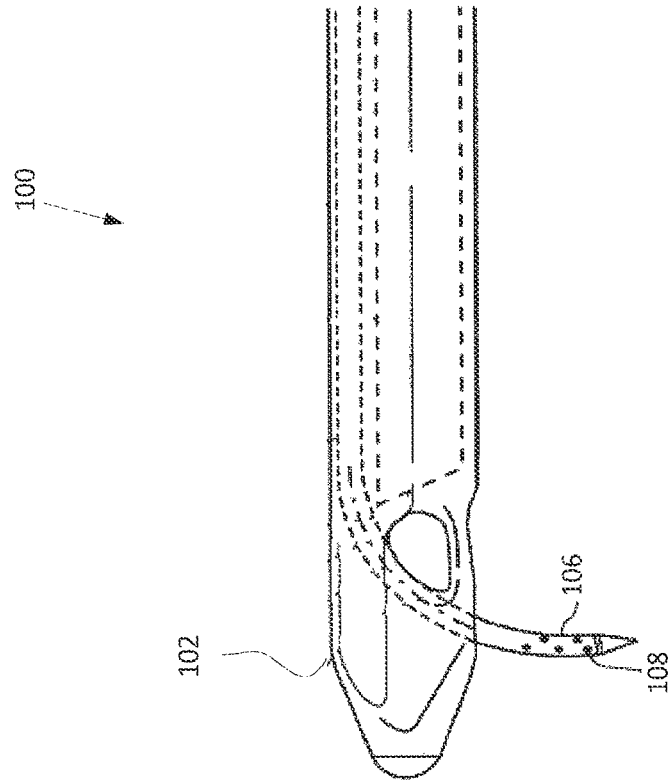

FIG. 1B shows a close-up view of the distal portion of the shaft of vapor system 100, including the vapor delivery needle 106 extending beyond the shaft and exposing the vapor delivery ports 108. Vapor delivery ports 108 may be arranged in a pattern that optimizes the delivery of vapor to tissue in a given application. For example, in a system designed for treatment of BPH the delivery ports 108 comprise three rows of four vapor delivery ports, the rows of ports being spaced at 120 degree intervals around the circumference of the needle, with one row of delivery ports facing distally from the front edge of the needle to ensure ablation of tissue adjacent to the prostatic urethra. In general, the vapor delivery ports can each have a unique diameter. In one embodiment the vapor delivery ports all have the same diameter. The system 100 can further include a lumen sized to accommodate an endoscope or camera to provide additional viewing and feedback to the physician. This endoscope or camera can provide a view of the distal end of the shaft, including a view of the vapor delivery needle when deployed.

Figure 1C:
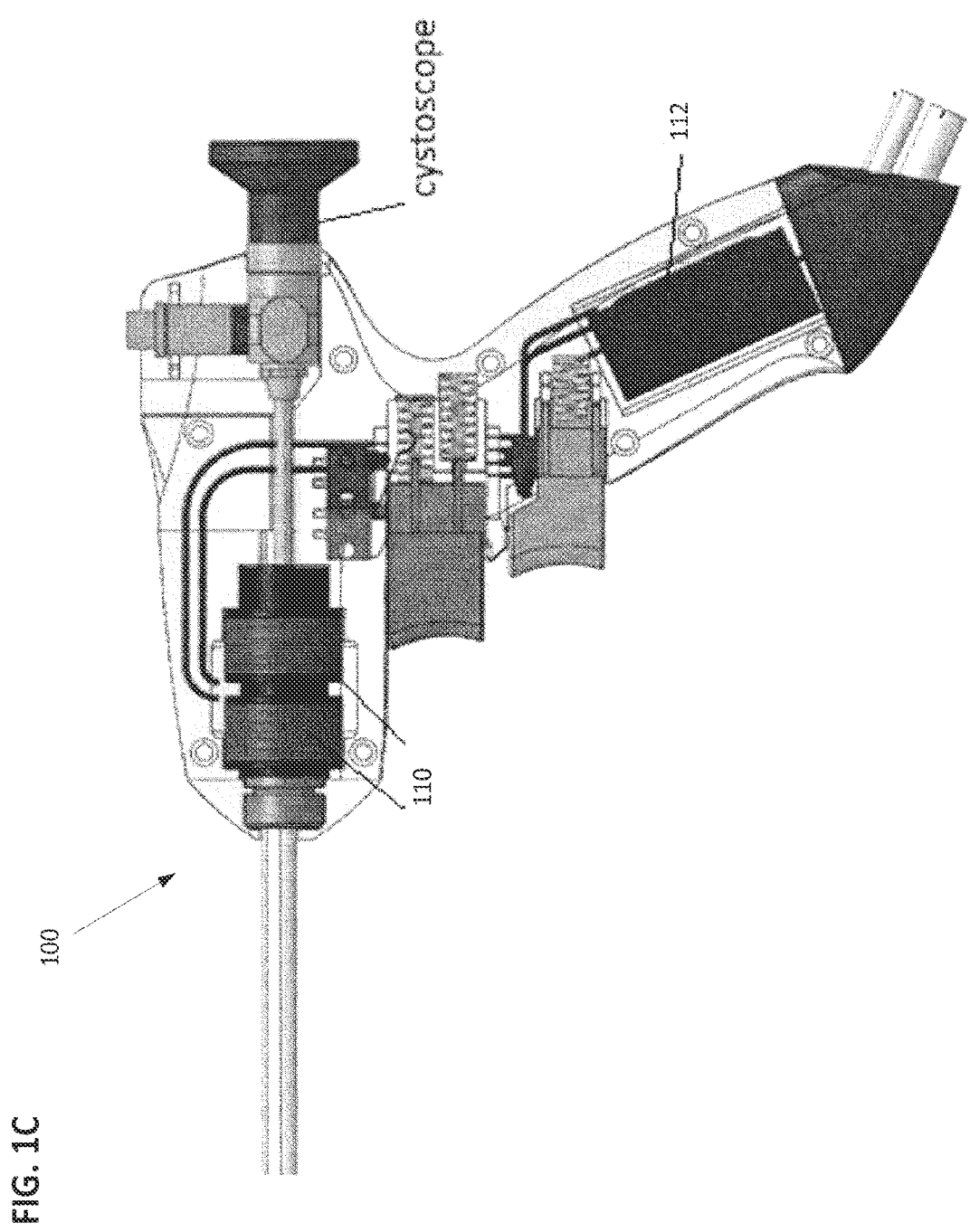

FIG. 1C is a cutaway view of the vapor delivery system 100, which illustrates solenoid needle driver 110 and vapor generator 112. The solenoid needle drive 110 can be configured to advance and retract the vapor delivery needle of the vapor delivery system, as will be described in more detail below. The vapor generator 112 is configured to produce a high quality vapor for delivery to the targeted tissue through the vapor delivery needle.

Figure 1D:
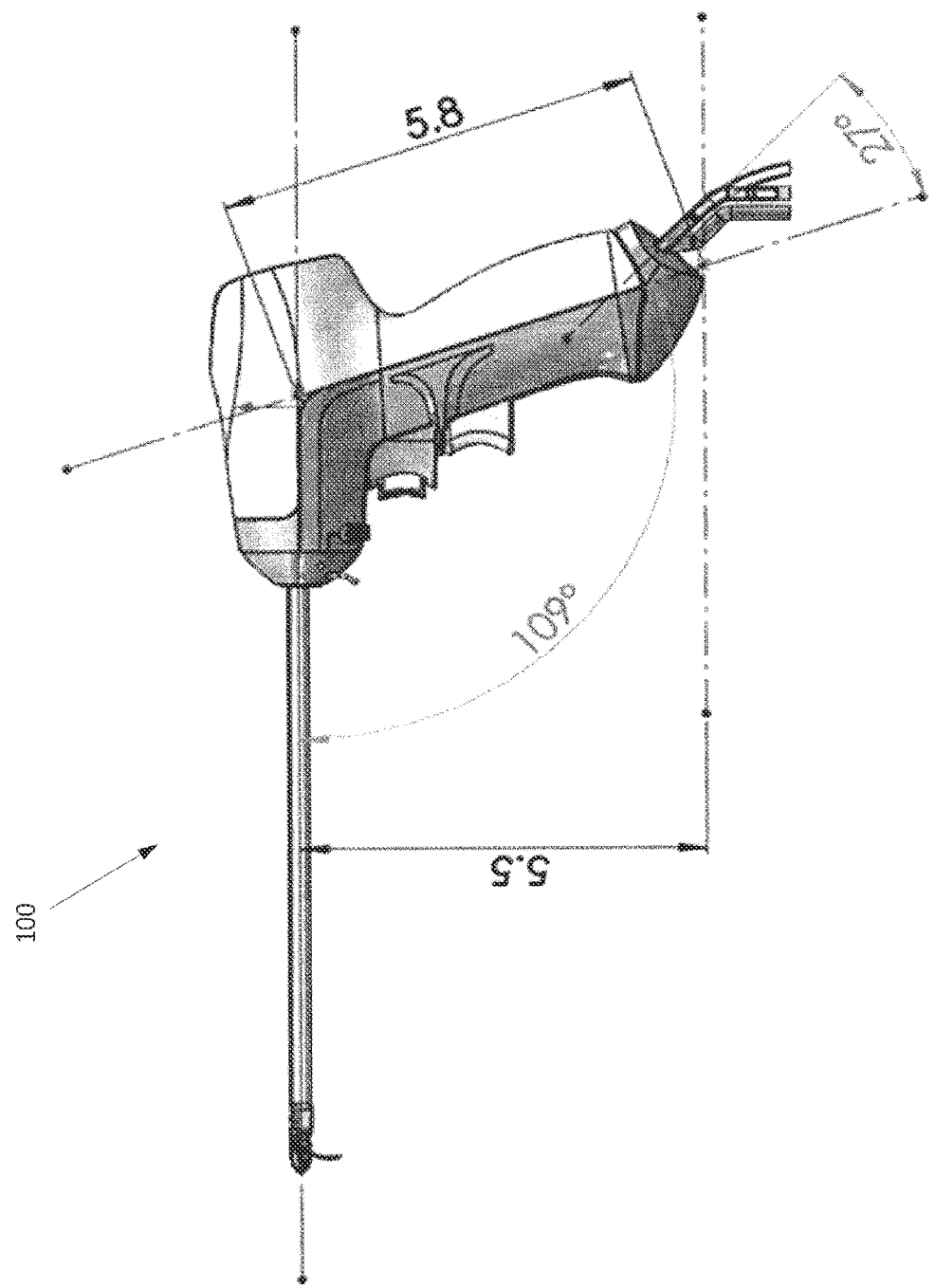
Figure 1E:
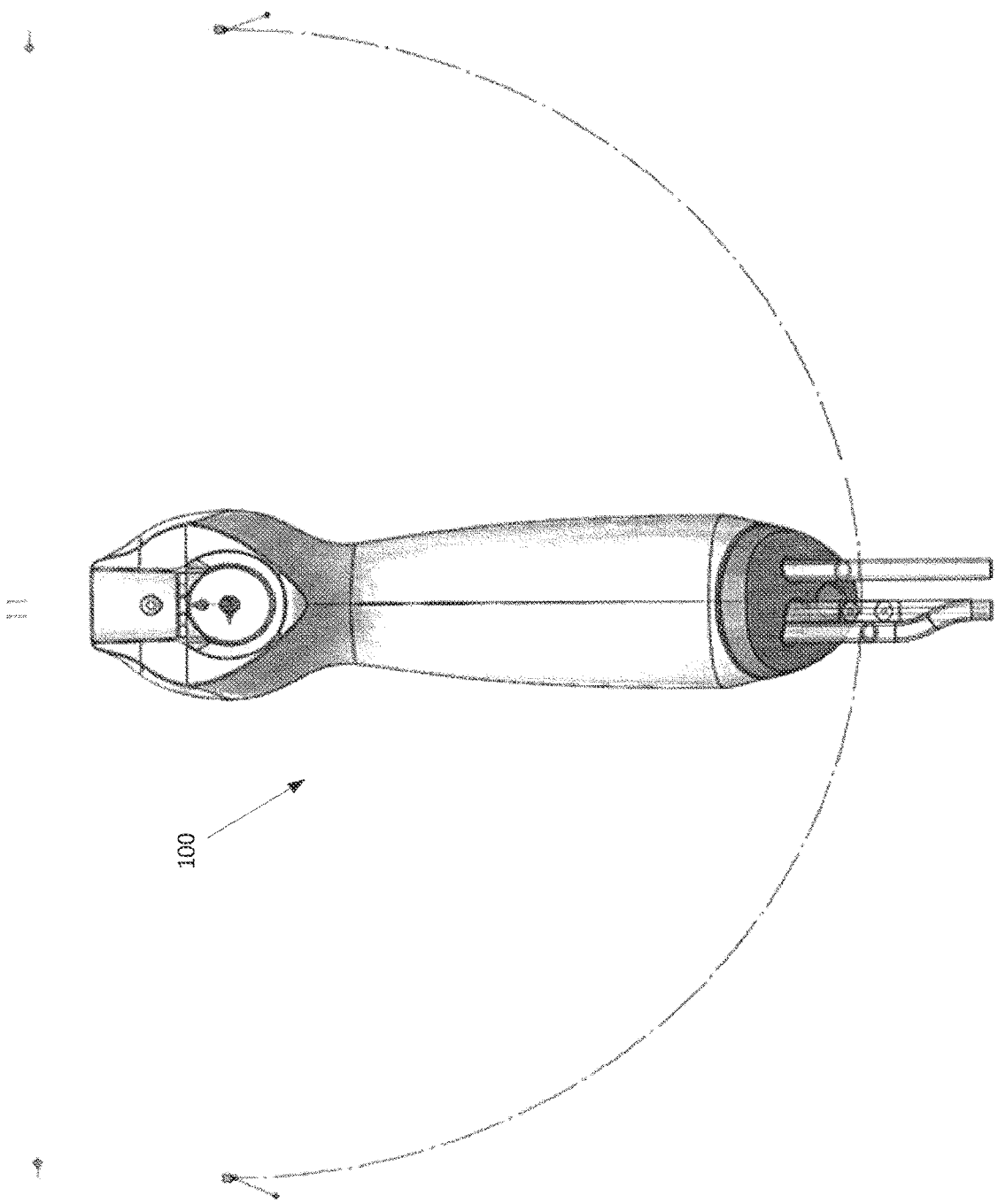

FIGS. 1D-1E show specific dimensions and angles of a handle assembly of the vapor delivery system, according to one specific embodiment. Earlier versions of the device incorporated a rotation mechanism allowing the physician to hold the device vertically while treating either of the lateral lobes. While the usability of this device was not impacted due to the working space between the knees of a patient, it did add to the complexity of the procedure due to multiple degrees of freedom in the system. The illustrated version of the device eliminates this mechanism simplifying the procedure (as well as simplifying its manufacture and reducing the cost). While the elimination of the rotating feature requires the physician to rotate the entire unit to access the lateral lobes it also allows for a reduction in size providing easier manipulation of the device during use.

Based on available anthropometric data, a male in the 5$^{th}$ percentile, in a typical lithotomy position in stirrups, has approximately 14 inches of space between his knees. During use of the vapor delivery device, the location of the device between the upper legs of the patient is based in large part on the length of the shaft of the device. This positions the device in an area of the upper leg that drove the design to the device, including 1) providing approximately 109° rake angle of the handle between the handle and the shaft. This feature allows for a comfortable angle of the wrist and easier trigger pulls while in both the pronate and supine positions. The incorporation of the rake angle allows for a slightly longer handle to accommodate physicians with larger hands while directing that portion of the device away from the patient's upper leg during rotation of the unit 90° to the left or right; 2) providing approximately 5.8 inches of handle length (FIG. 1D) resulting in an approximate 11 inch swing diameter (FIG. 1E); 3) providing an additional 27° take-off of the tube set and cable to provide more clearance to the patient's upper leg; and 4) providing a distal location, symmetric design, and electric activation of the retract button. Previous versions of the device utilized a lever on the back of the device requiring in excess of 10 lbf to activate frequently resulting in an unstable device during this step. Due to its symmetry, the new design is easily activated with the index finger of either the right or left hand with an approximate force of ½ lbf leaving the device completely stable during its use.

Figure 2:
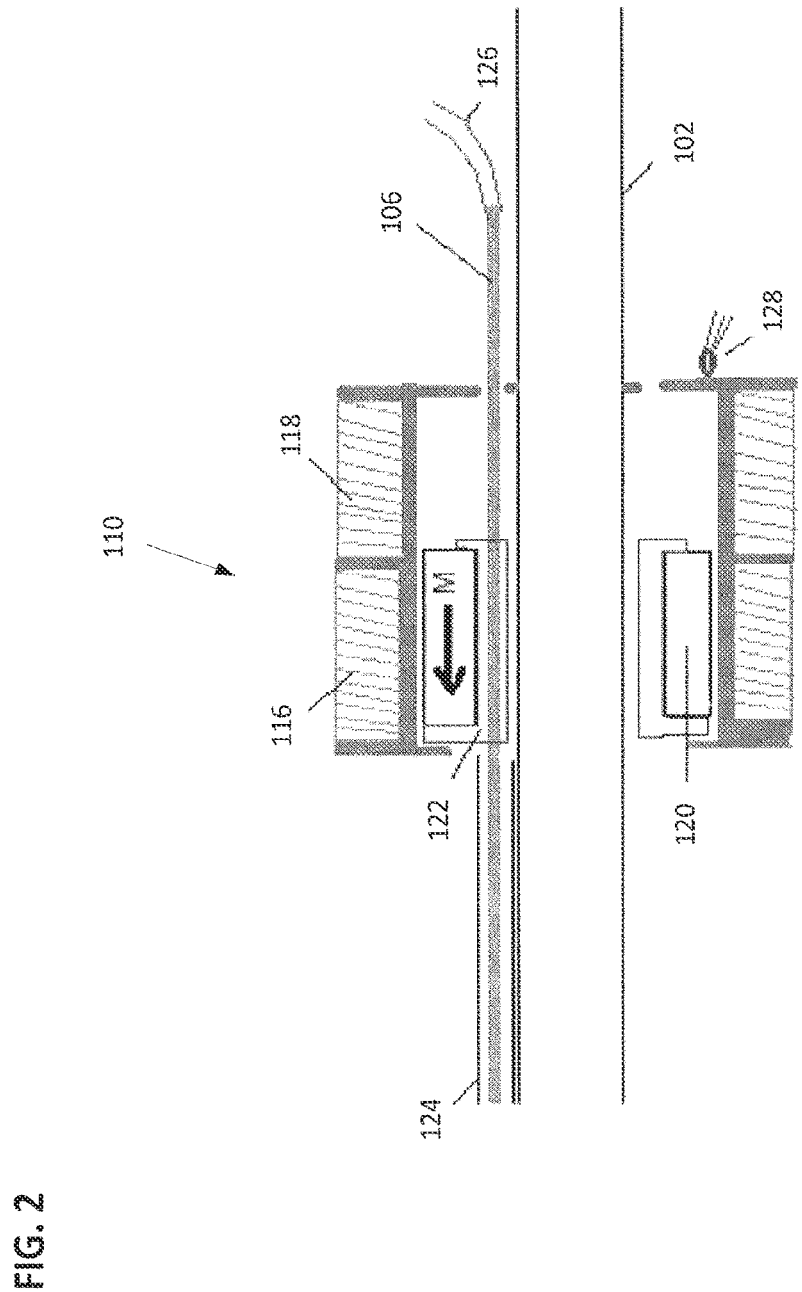
FIG. 2 is a close-up view of a distal portion of the vapor delivery system.
Figure 3:
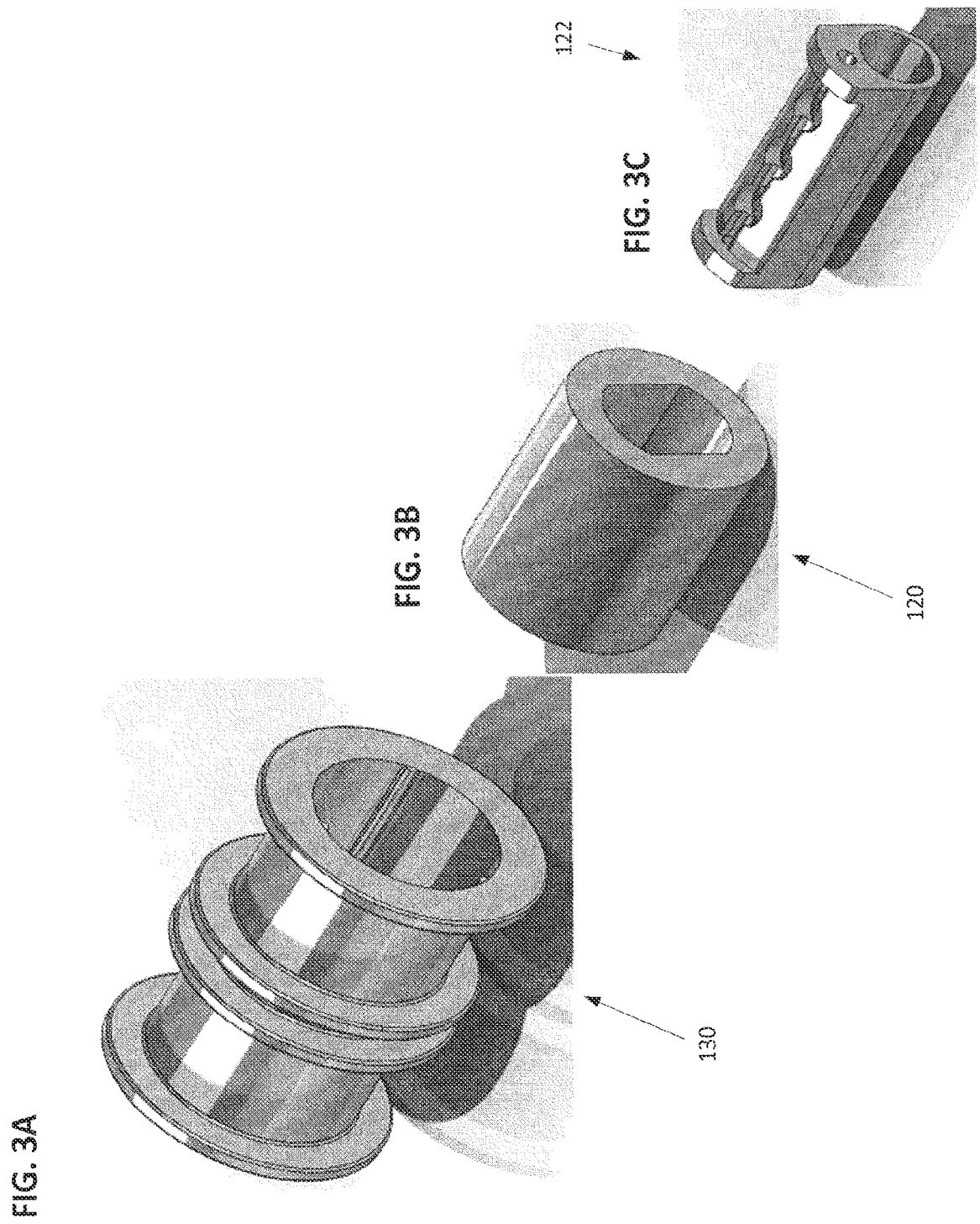
FIGS. 3A, 3B and 3C show an exploded view of a solenoid needle driver.

FIGS. 2-5 describe features and functionality of the solenoid needle driver of the vapor delivery device. FIG. 2 is a cross-sectional schematic diagram illustrating the functionality of solenoid needle driver 110. The solenoid needle driver includes the vapor delivery needle 106, a pull winding 116, a push winding 118, a magnet 120, a needle holder 122, a needle tube 124, a flexible tube 126, and a magnetic field sensor 128. In FIG. 2, the solenoid needle driver is shown in its fully advanced position. The vapor delivery needle 106 can be rigidly attached to magnet 120 via needle holder 122. The magnet can then be moved laterally by generating magnetic fields in the push and pull windings 116 and 118, as will be described in more detail below. Magnetic field sensor 128 senses the intensity of the magnetic field produced by the push and pull windings.

FIGS. 3A-3C show an exploded view of additional features of the solenoid needle driver. FIG. 3A shows a solenoid coil holder 130, which holds the push and pull windings of FIG. 2. The magnet 120 of FIG. 3B slides within the solenoid coil holder 130 of FIG. 3A, depending on the magnetic field generated by the coil windings. The needle holder 122 of FIG. 3C attaches the vapor delivery needle to the magnet.

In one embodiment, the magnet can be made from grade N48 Neodymium-Iron-Boron, having residual induction of about Br≈1.4 Tesla. The magnet of FIG. 3 has an inside surface that is shaped to fit over and snap onto the needle holder. Because the magnet is an oriented material having a high coercive force, the entire magnet is uniformly magnetized along its axis. The force on the needle driver is therefore proportional to the volume of the magnet, and the extra magnet material that forms the sides of the inside surface increases the needle driver force. The needle holder can include holes configured to receive adhesive to rigidly attach the vapor delivery needle to the holder.

Figure 4:
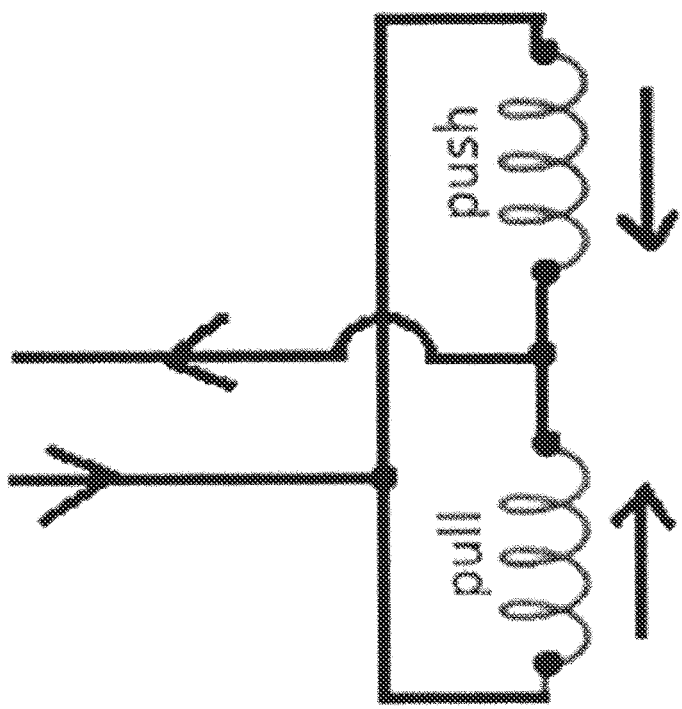
FIG. 4 is a picture of a solenoid needle driver.
Figure 5:
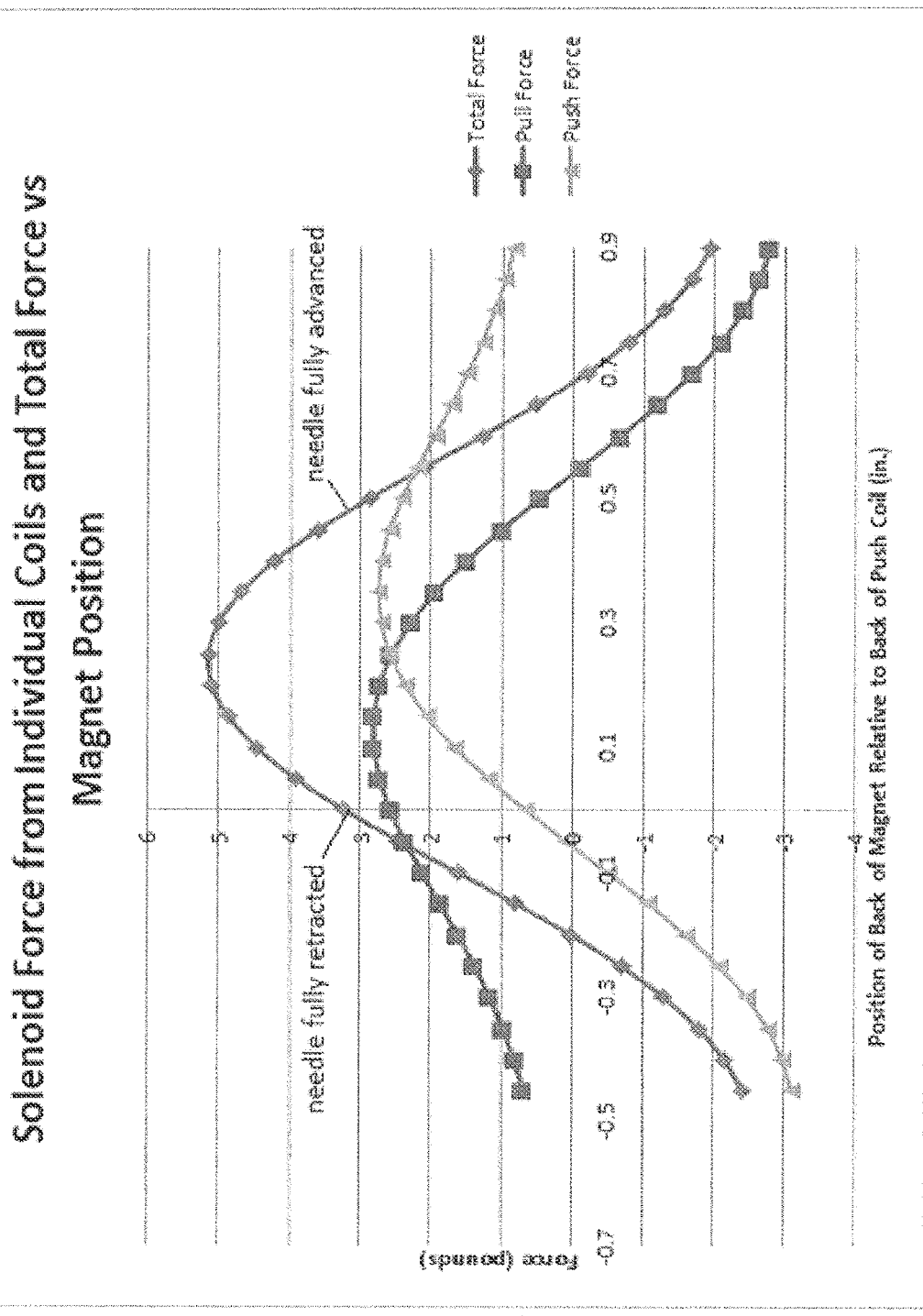
FIG. 5 illustrates the current flow through the solenoid needle drive to deploy the vapor delivery needle.
Figure 6:
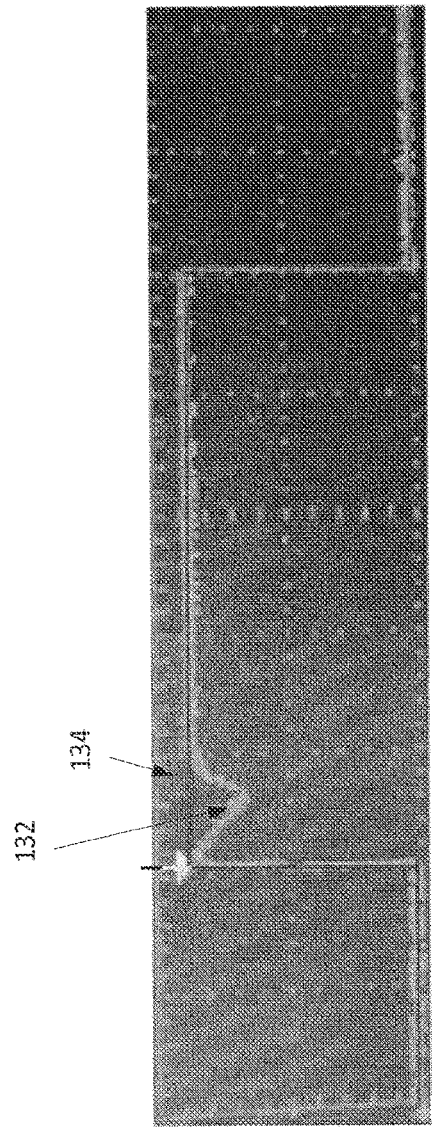
FIG. 6 shows the measurement of back current from a moving magnet to determine magnet deployment/position.

Referring to FIG. 2, the solenoid includes push and pull windings that are configured in a push/pull configuration relative to the magnet and needle holder. In the fully retracted needle position, the back end of the magnet 120 is aligned with the back end of the push winding 118. The front end of the magnet extends into the pull winding 116 in this fully retracted needle position. To advance the needle into the advanced needle position, current is passed in opposite directions in the push and pull windings, as shown in FIG. 4. The push winding sets up a magnetic field that repels the same polarity magnet out of the winding. Because of the repulsion, the magnet is not in stable equilibrium along the push coil axis, and is prone to lateral movements that could increase contact between the magnet and its surroundings, and increase frictional resistance to axial advancement. The pull winding creates a magnetic field that attracts the magnet into the pull winding. The pull winding attracts the magnet to the axis of the coil, and thereby removes the instability of the push winding. The combination of push and pull windings approximately doubles the force exerted by a single winding. The push/pull pair of windings also makes the retract force identical to the advance force simply by reversing the direction of current to the coil pair, as seen in FIG. 4.

In one embodiment, the push and pull windings are each wound with approximately 400 turns of AWG #30 magnet wire, each coil having a DC resistance of about 10 Ohms. Current can be supplied to the solenoid coils by a 24 volt DC power supply that is activated for about 0.05 sec during advance or retract. Since the push and pull windings are connected electrically in parallel, the resistance of the coil pair in this example is 5 Ohms and the solenoid current is about 24/5=4.8 amps. The ON time is so brief that the winding temperature does not increase significantly during activation. The needle advances/retracts through its full range of about 11 mm in less than 0.020 seconds.

The axial force exerted by the solenoid windings on the magnet may be computed from the expression for the force on a magnetic dipole exposed to a field gradient. The magnetic field from the coils and its gradient may be computed from the law of Biot and Savart. The force on a point dipole may be integrated over the magnet volume to give the net force acting on the needle driver. This calculation is plotted in FIG. 5 for a magnet that is 10 mm inner diameter by 15 mm outer diameter by 20 mm long, and push/pull windings having 408 turns of #30 copper wire. The overall range of movement of the magnet is indicated in the figure. In this range the force is in the 2.5-5 pound range, and peaks at the mid-point of its travel range. The net force on the needle driver is this force minus the frictional forces encountered along its travel. The entire curve in FIG. 5 scales up and down in proportion to the solenoid current. Many forcing scenarios are possible, including varying the force along the needle trajectory, and making the retract force different from the advance force.

The forces on the magnet can be altered by selective placement of magnetic materials along its path of travel. For example, a steel ring or washer may be placed at the distal end of the solenoid needle driver to provide a holding force on the magnet after the solenoid current is turned OFF. The emergency needle release ring shown in FIG. 1A may serve the same purpose when it is made of magnetic steel. The initial force exerted by the solenoid windings during retraction must be strong enough to overcome the holding force of the washer.

The solenoid needle driver of FIGS. 2-5 provides the ability to precisely sense the position of the vapor delivery needle. In one embodiment, the magnetic field sensor 128 can be placed in the proximity of the needle driver magnet that will provide a voltage output that is to proportional to the magnetic field produced by the magnet. The magnetic field sensor can be located such that the magnetic field has a monotonic relationship to the magnet position (for example adjacent the proximal end of the magnet when in the retracted position, as seen in FIG. 2). Since the magnetic field of the magnet is large compared to the magnetic field of the solenoid windings and other stray magnetic fields, the position of the magnet, and thus the position of the needle, can be uniquely determined by the magnetic field sensor at any time before, during, and after needle deployment. Delivery of vapor to an under deployed needle can thereby be prevented by a controller of the vapor delivery system. The magnet position versus time during needle deployment may also be monitored by the controller. Complete but slow or jerky movement of the magnet may indicate excessive friction in the system or binding of the magnet or needle.

In another embodiment, an indication of magnet/needle position can be provided by the back EMF that the magnet exerts on the solenoid windings. When the solenoid is energized with a constant current source, the back EMF appears as a dip in the voltage across the solenoid whenever the magnet moves. The current/voltage/back EMF can be measured with a current sensor in the solenoid, or alternatively, in the generator that provides power to the solenoid. When the solenoid is energized with a constant voltage, such as a 24 Volt DC power supply, the back EMF manifests as a dip in the current flowing through the solenoid circuit. FIG. 6 shows a normal solenoid current 132 (including the dip in current) when the needle driver magnet deploys normally, and a failed solenoid current 134 (showing a constant current) when the magnet is prevented from moving. The back current only occurs when the magnet is moving, indicating that the magnet and needle driver are fully deployed in about 10 msec. The current remains ON for one sampling cycle of the computer, or 50 msec.

To isolate the back EMF, the current sensor output can be band pass filtered to eliminate the DC level associated with non-deployment, and eliminate fast transients when the current turns ON and OFF. Amplification of the filter output results in a pulse that may be interpreted as an ON bit when sampled by the controller. If no back current pulse is measured after solenoid power is switched ON, the magnet has not moved, and the operator is alerted. Further analysis of the back current wave form may provide a refined diagnostics of the magnet and needle movement. For example, the duration of the back current indicates how long the magnet was moving, which is indicative of how far the magnet has moved. Noise or jerkiness of the wave form may indicate points of increased friction along its travel.

FIG. 7 shows a detailed view of the vapor generator 112 of the vapor delivery system of FIG. 1C. The vapor generator 112 can include an inner vapor coil 136 and an outer RF coil 138 of conductive wire that surrounds the inner vapor coil. Sterile water can be introduced into the inner vapor coil, and RF current applied by a RF generator 139 to leads 140 of the outer RF coil can inductively heat the inner vapor coil and generates a steam or vapor. The inner vapor coil can be connected to a supply of sterile water through a plastic tube that extends from the inner coil to a fluid source.

In a preferred embodiment, the windings of the vapor coil can be constructed from Inconel, a nickel/chrome stainless steel metal tubing. For example 18 gauge RW Inconel 625 tubing or 18 gauge thin wall (TW) Inconel 625 tubing are preferred. Alternating, RF frequency currents flowing in the outer RF coil of FIG. 7 induce circumferential current flow in the body of the inner vapor coil. It is important to have good electrical contact between the windings of the inner vapor coil.

In this case, the heating element may be modeled as a transformer having an N turn outer RF coil and one turn inner vapor coil. The current flowing in the inner coil may be approximately N times the current flowing in the RF coil. The induced inner coil current produces heat in the inner coil via Ohmic ($I^2r$) heating that converts water flowing in the inner coil to steam. As described above, it is advantageous for the individual coil windings of the inner vapor coil to be in physical contact, which can be achieved by soldering or welding the individual windings together to ensure good electrical contact between windings. One distinct advantage of Inconel 625 coiled tubing is that the oxide layer that forms on its surface is sufficiently thin to freely pass RF current between adjacent windings of the inner vapor coil, with no requirement for soldering.

Another advantage of Inconel is that it is an intrinsically non-magnetic material. While magnetic permeability can enhance the coupling between the RF coil and inner coil, the magnetic properties of stainless steel tubing are not consistent from lot to lot of tubing. Because consistency in calorie output from device to device is very important, non-magnetic tubing is preferred in this application. Stainless steels like 304 may be annealed to eliminate magnetic properties. Another advantage of Inconel 625 tubing is that its electrical properties are almost independent of temperature over the range (room temperature to 350° C.) experienced by inductive heating of the inner coil. Stainless steels such as 304 or 316 not only have a much more substantial change in electrical properties with temperature, but due to the multiphase make up of these materials, temperature cycling can produce history dependent and unpredictable changes in electrical properties, a small but significant effect.

The calorie output of the vapor delivery device of this disclosure is related to the power input of the RF generator during therapy delivery through an efficiency coefficient. Calorie output will be consistent from shot to shot if the power delivered is a constant, independent of changes in component values due to the thermal cycling of the device. Calorie output will be consistent from device to device if the input power is always the same for a given therapy, and if the efficiency coefficient is consistent from device to device. Device to device consistency is achieved through consistency of device manufacturing. In addition, consistency improves as the power coupling efficiency approaches 100%, provided that the input power is held constant. In other words, variations in device parameters have a diminishing effect on output as the percentage of the constant input power delivered to the output approaches 100%.

In one embodiment, the RF generator is designed to servo the electrical power delivered at its output to a set value by measuring voltage and current at the output, computing the output power, and adjusting output voltage in real time to keep the output power equal to the set power. The percentage of the input power that is delivered to the vapor coil as Joule heating can be computed by analyzing an equivalent circuit of the vapor delivery system, in which current is inductively coupled from the RF coil to the vapor coil through a mutual inductance, M.

The elements can be defined as:
V=rf generator voltage amplitude in volts, delivered at frequency f in MHz
$I_1$=rf current flowing into the delivery device in amps
$I_2$=rf current flowing in the vapor delivery coil in amps
$R_c$ and $R_1$ are the ac resistances of the cable and rf coil respectively in Ohms
$L_c$ and $L_1$ are the inductances of the cable and rf coil respectively in μH
$R_2$ is the circumferential ac resistance of the vapor delivery coil in Ohms
$L_2$ is the inductance of the vapor delivery coil in μH
M is the mutual inductance between the rf coil and vapor delivery coil in μH
where $M^2 = c\ L_1 L_2$, $0 < c < 1$
c is the transformer coupling coefficient between the rf and vapor coils The electrical power coupling efficiency is defined as the ratio of Ohmic heat generated in the vapor delivery coil to the input power:

$$\eta = <I_2^2 R_2>/<I_1 V>,\ 0 < \eta < 1$$

Figure 7:
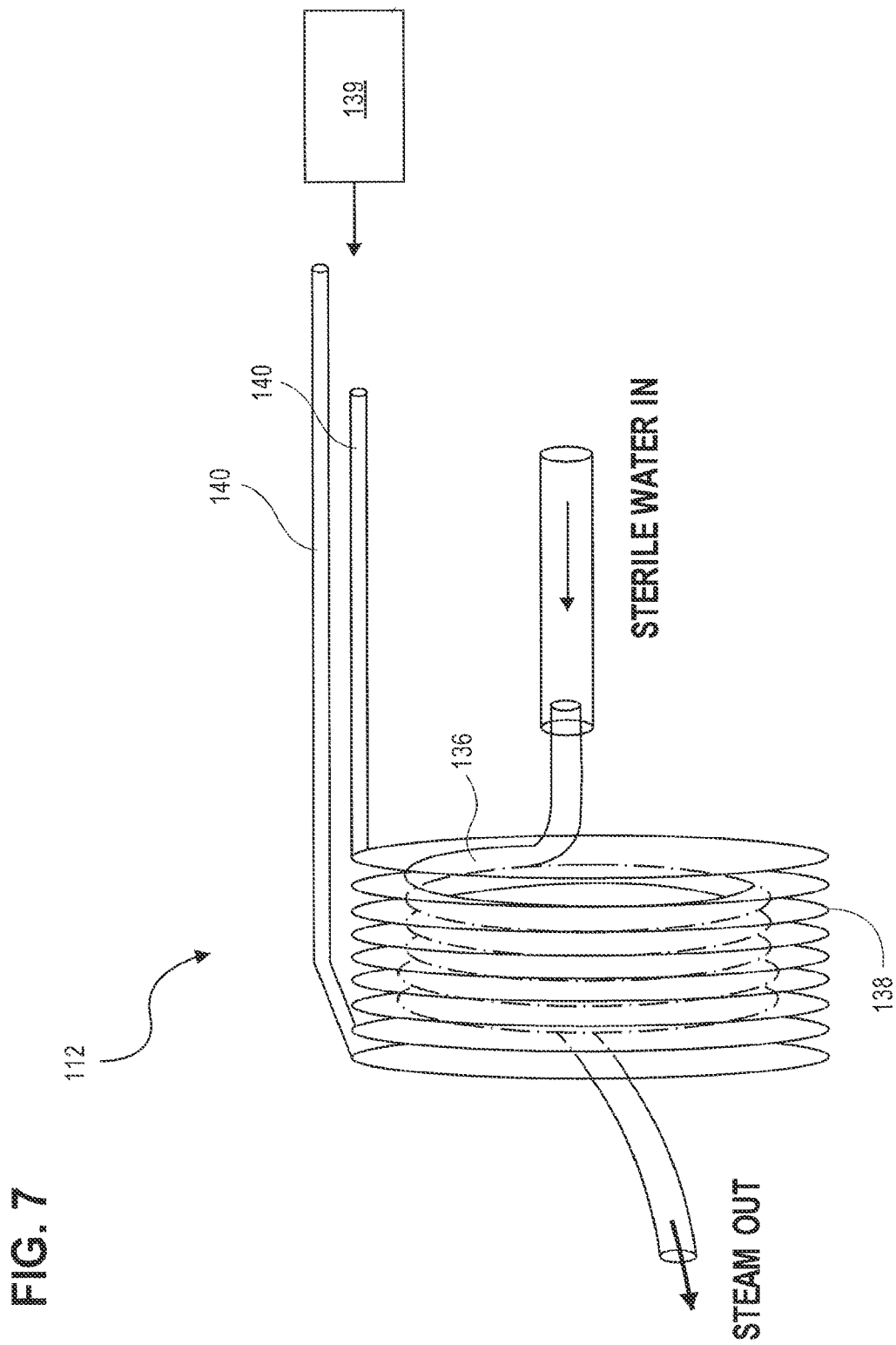
FIG. 7 shows one embodiment of a vapor generator.

And the brackets < > represent the average over one cycle of the sine wave input at frequency "f". The design goal is to make the electrical power coupling efficiency, η, as close as possible to unity (100%). Using standard mathematical analysis, the circuit equations for FIG. 7 may be solved to yield an expression for η in terms of the other circuit parameters:

$$\eta = xQ_2/(1+xQ_2+Q_2^2)$$

where $x = 2\pi f c L_1/(R_c+R_1)$ $$Q_2 = 2\pi f L_2/R_2$$

Where x comprises parameters of the input circuit and coupling coefficient, and $Q_2$ comprises parameters solely of the secondary vapor delivery coil. Efficiency is plotted in FIG. 10 as a function of $Q_2$ for fixed values of x. It is seen that efficiency has a peak value when $Q_2=1$ for all values of x, and that efficiency increases with increasing x. One way of appreciating this fact is that when the electrical resistance if the inner coil is too high, induction of eddy currents will be small with little heat produced. Conversely, when the electrical resistance of the inner coil is too small, the $I_2^2 R_2$ Ohmic heat will be small. The peak in the curve is expected.

In a practical design of a vapor delivery system, the heating element may comprise nested solenoid coils, where the inner vapor coil is a single turn winding. Formulas for the inductance of solenoid coils and the mutual inductance of nested solenoid coils may be found in the literature, completing the solution for efficiency. These formulas require numerical integration. However, with the nested coils are long and thin, closed form solutions are available. In this approximation, $Q_2$ is:

$$Q_2=2\pi f\mu_0\mu_2Dt/(4\rho) \text{ for a single turn solenoid coil}$$

where $\mu_0$=permeability of free space=4πx$10^{-7}$ Henries/meter $\mu_2$=relative permeability of the vapor coil D=vapor coil diameter in meters t=smaller of the vapor coil tube wall thickness or the skin depth at frequency f in m.

ρ=electrical resistivity of the inner coil tubing in Ohm-meters

The combination of the parameters comprising $Q_2$ are chosen, in a preferred embodiment, to force $Q_2$≈1, thereby optimizing power coupling efficiency. The relative permeability of the inner coil, $\mu_2$, is equal to unity for non-magnetic materials such as Inconel and annealed 300 series stainless steels.

While the operating frequency may be adjusted to set $Q_2$=1, common medical RF generators have operating frequencies in the 400 to 500 kHz range. Complications such as power being radiated from the heating element occur at higher frequencies, and efficiency starts to droop at lower frequencies. Diameter and tubing wall thickness may be adjusted within the system constraints, and materials having appropriate electrical resistivity may be chosen to bring $Q_2$ as close to unity as possible. In a preferred embodiment, the outside diameter of the inner coil is 9 mm, the wall thickness is 0.2 mm, the material is Inconel 625 having resistivity of 1.32 μOhm-m, and the operating frequency is 440 kHz, yielding a computed $Q_2$ of 1.2, and a measured $Q_2$ close to unity. Numerical evaluation of the inner coil inductance brings the computed and measured values of $Q_2$ to even closer agreement.

Parameters on the input side of the heating element circuit may be chosen to maximize the value of x, within practical constraints. For example, is easy to increase $L_1$ by using many turns of fine wire in a single layer RF coil, or by creating a multiple layer coil of a larger diameter wire. In practice, heating powers of 100 Watts or more may be needed to deliver adequate vapor therapy. AC currents in the range of 5 to 20 amps may be required to deliver adequate power, so that the wire chosen for the RF coil must have a current carrying capacity in this range. Wire that is too small in diameter for a given RF current will show a dramatic increase in resistance and temperature over time during therapy. From the formula for x, an increase in resistance $R_1$ drives the value of x back down.

For example, in one embodiment it was found that a single layer coil made with AWG #22 Litz wire gave higher calorie output than coils of the same length made from either #20 or #24 Litz wire. Multiple layer coils may be practical to a point. The coupling constant, c, falls off as the separation between the RF and vapor coils increases. In an example of long solenoid coils, c is equal to the ratio of the cross sectional areas of the inner and outer coils, so falls off with the square of the diameter of the outer coil for a fixed vapor coil diameter. Another practical limitation is that the impedance of the RF coil circuit increases with increasing RF coil inductance $L_1$, requiring higher voltages to produce a given current in the RF coil. High voltage has practical and regulatory limitations in medical applications. Cable resistance also has practical limitations, as bulky cables made with large diameter copper wire are not tolerated in clinical practice. Working vapor delivery systems having x>15 and efficiency between 75%-90% have been achieved.

The overall efficiency of the vapor delivery system is less than 100%, even when the electrical power coupling efficiency approaches 100%. This is due to heat lost to conduction, convection and radiation from the heating element and delivery tubing and needle, and to Ohmic heating by currents in the RF coil, which is partially conducted or radiated away from the inner coil. The thermal design of the delivery device minimizes these losses to about 8% of the heat generated in the vapor coil. The overall efficiency of the vapor delivery system is defined by the equation:

$$\text{Calories output from the needle} \times (4.186 \text{ Joules/calorie})/\text{treatment time} = \varepsilon P_{in}$$

where $\varepsilon$=overall power coupling efficiency
$P_{in}$=constant power input from the Rezūm generator The calorie output from the vapor delivery needle is readily measured by delivering the vapor to a known quantity of water in a calorimeter. For delivery devices used in BPH therapy the mean measured calorie output was 208 calories. The BPH treatment therapy time for these devices is 9 seconds. Delivery devices constructed in our lab have achieved 208 calories output with as little as 115 Watts input power, for an overall efficiency (computed from the above equations) of $\varepsilon$=84%. The first commercial delivery devices achieved 208 calories with an input power of 132 Watts for an overall efficiency of $\varepsilon$=73%.

Thermal losses from Ohmic heating in the RF coil may be minimized by insuring good thermal contact between the RF and inner coils. This is achieved by minimizing the thickness of electrical insulation between the two coils, while still meeting electrical safety requirements. A good result is found with the insulation being a polyimide (kapton) tube with wall thickness of 0.1 mm. Similarly, using a thin wall hypotube for the vapor coil allows heat generated in the rf coil to better conduct to the water in the inner tube. The trade-offs here are mechanical integrity of the hypotube and keeping $Q_2$ close to unity.

The electrical power coupling efficiency is defined as the ratio of Ohmic heating power delivered to the inner vapor coil tubing divided by the RF generator input power. Further losses of calorie output from the device occur with heat lost to conduction, convection and radiation within the delivery tool handle and along the vapor path through the delivery device probe. These losses manifest in condensation of steam along the vapor path. The large latent heat of vaporization is lost from the delivery device output when steam condenses within the device. The condensed hot water may be delivered to the tissue, but with a much smaller heat content than steam.

Thermal losses may be minimized by one or more of the following measures:
1) Thermal insulation around the heating element. Air is a good and inexpensive insulator. In some embodiments, low mass baffles may be added to inhibit convection.
2) Metallic reflectors on the inside surface of the handle. The metallic reflectors can reflect thermal radiation back to the heating element. These reflectors must avoid eddy current heating in the reflectors (e.g., foil with no continuous current paths). In some embodiments, the reflectors may be diced into squares to break up current paths.
3) Minimize the length and thermal conductivity of outlet tubing. Tubing connecting inner coil outlet to vapor delivery needle can be shortened or minimized.
4) Air gap around the vapor delivery needle.

The above discussion of calorie delivery efficiency assumes a consistent and reliable flow of water to the inner coil for conversion into vapor. In practice, the water line tubing is compliant to some degree, and it can store a small amount of water as it stretches under pressure at the beginning of therapy. Since the sterile water is being pumped at a controlled flow rate, the stored water subtracts from the water delivered to the inner coil, reducing the calorie output of the delivery device at the beginning of therapy. The water stored in the tubing compliance is released at the end of therapy, however RF power is OFF during this release so it does not contribute to calorie output.

The length of time that flow is diverted into the tubing compliance depends upon the product of the tubing compliance and water line plus inner coil flow resistance. The flow resistance of the inner vapor coil is much larger than the flow resistance of the water line because the water line is sized to fit over the inner coil outside diameter, and flow resistance increases as the inverse fourth power of tubing inside diameter. A slight reduction in the inside diameter of the inner coil can increase the time that it takes the water flow rate in the inner coil to reach its equilibrium value, and decrease the calorie output of the delivery device.

In practice it is found that the flow of water to the inner coil and the calorie output of the delivery device is nominal when the water line is made of rigid, non-compliant materials such as PTFE (Teflon). Somewhat more compliant materials such as high density polyethelene (HDPE) and low density polyethelene (LDPE) show only slight reduction in calories, while more compliant materials such as PVC can have a significant reduction in calorie output at the beginning of therapy unless the tubing wall thickness is greatly increased to decrease its compliance.

Increasing the inside diameter of the inner vapor coil reduces the calorie dependence on water line tubing compliance. In one example, when the inner coil inside diameter was increased from 0.84 mm to 0.89 mm, full calories were recovered with a thick PVC water line material. In production, the inner coil tubing inside diameter must be specified tightly to avoid accidental increases in flow resistance due to under size inside diameter. Plug drawn tubing controls both the inside and outside diameters of thin wall hypotubes. In this process the tubing inside diameter is held to a tolerance of +/−0.0005" or +/−0.0127 mm.

Compliance of the tubing that connects the inner coil to the vapor delivery needle must also be minimized to avoid condensation due to volume expansion in this tube, and to prevent oscillations that inhibit the exit of vapor from the output needle holes. Silicon is a preferred material for the connecting tube because it withstands the high vapor temperature. In some embodiments a fiberglass mesh is placed over the tubing outside diameter to prevent its expansion. In another embodiment, a metal braid is co-extruded into the wall of the silicon tube to make it non-compliant. In another embodiment, the heating element is placed in the barrel of the delivery device to minimize the length of any tubing connecting the heating element to the vapor delivery needle.

Figure 8A:
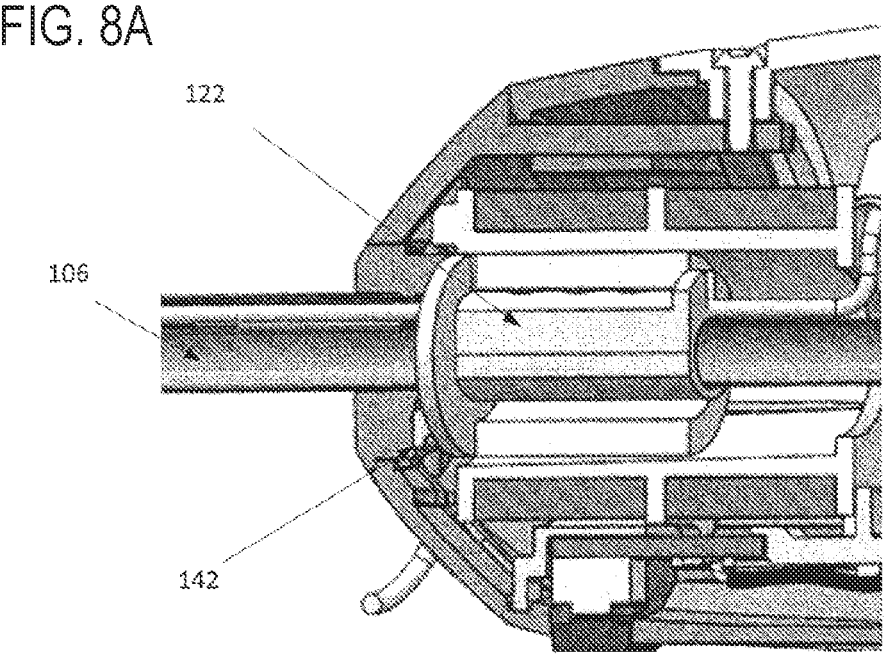
FIGS. 8A, 8B, 8C and 8D show a shipping pin configuration that prevents the vapor needle of the vapor delivery system from moving during shipping of the system.

FIGS. 8A-8D show a shipping pin mechanism that prevents the vapor needle of the vapor delivery system from moving during shipping of the system. Referring to FIG. 8A, a needle holder 122 is bonded to the vapor delivery needle 106. The needle holder 122 further includes a hook feature 142 adapted to capture a shipping pin, which will be described below.

Figure 8B:
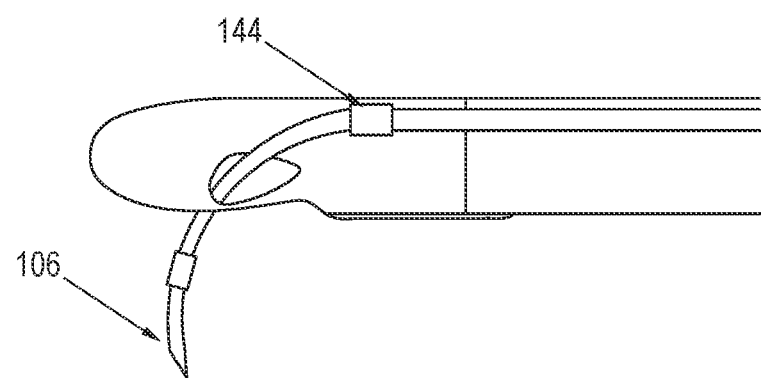

Referring to FIG. 8B, the vapor delivery needle 106 further includes a needle seal 144, which is configured to seal the lumen in the shaft of the device through which the needle is advanced. The needle seal prevents fluid and other debris from entering the lumen.

Figure 8C:
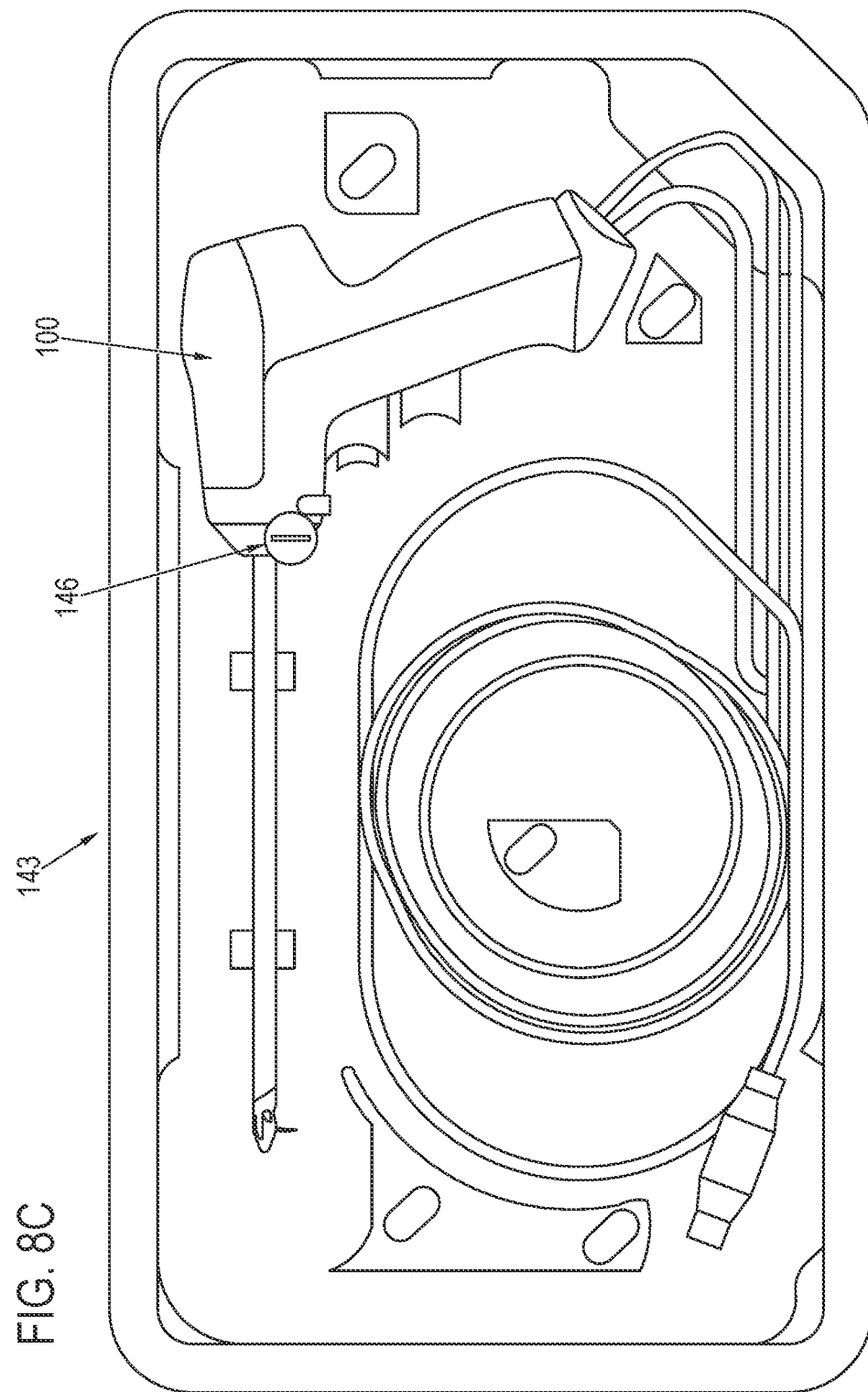
Figure 8D:
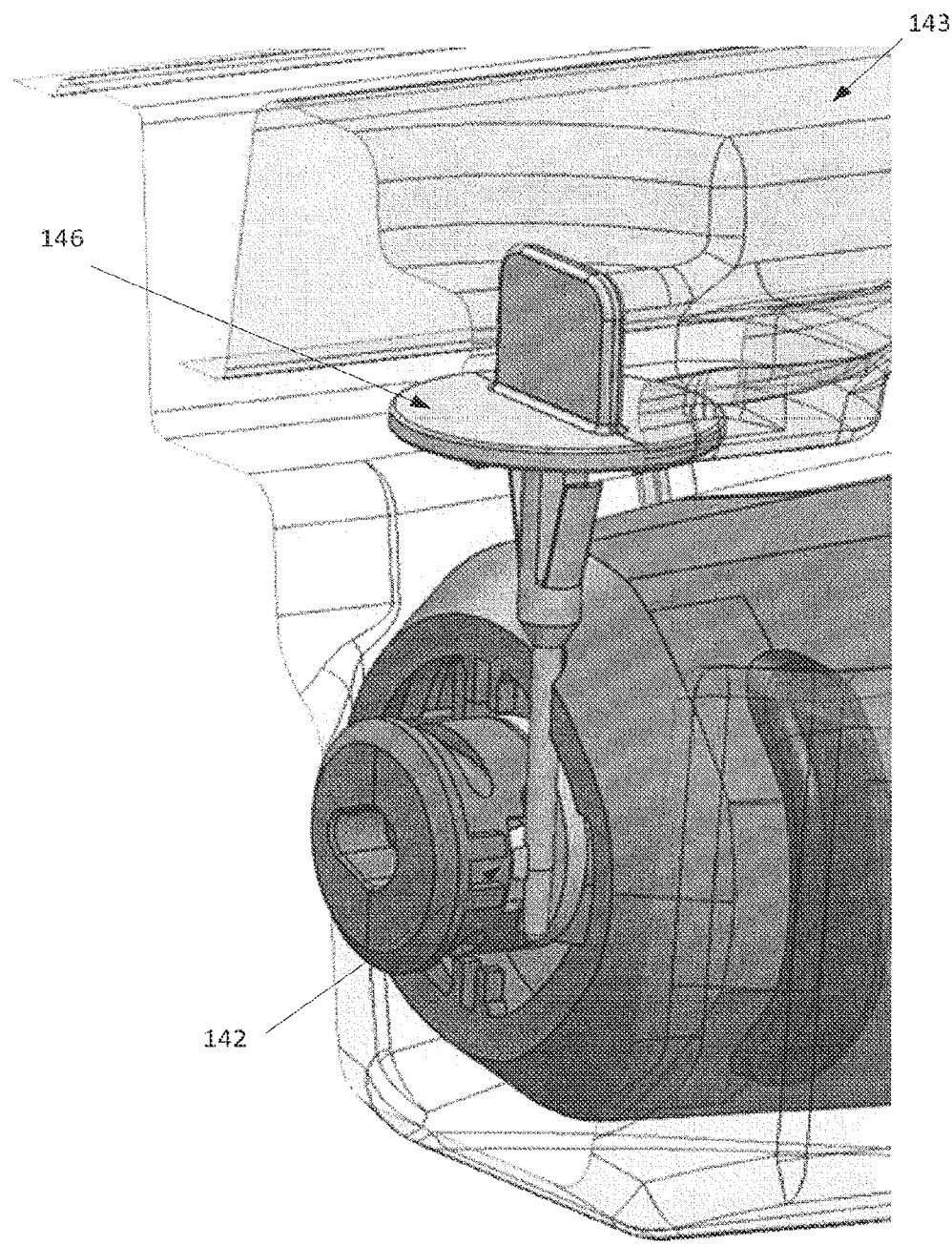

FIG. 8C shows the vapor delivery system 100 packaged in a shipping package 143. As shown, the vapor delivery needle is advanced beyond the distal tip of the device, and a shipping pin 146 is placed through an opening in the package into the hook feature of the device to lock the position of the needle in place. FIG. 8D shows a closer view of the shipping pin 146, illustrating how the shipping pin is advanced through the shipping package 143 down into the hook feature 142 of the vapor delivery system.

The shipping pin mechanism comprises a pin, insertable through a tray retainer of the shipping packaging, and into the vapor delivery system. Inside the vapor delivery system, the pin aligns and captures the hook feature of the needle holder such that the needle holder cannot move during shipping. Since the needle holder is bonded to the needle, this prevents the needle from retracting into the shaft of the device during shipping. This is necessary as retraction of the needle during distribution is unacceptable, due to the fact that the needle has a set curved shape at the emitter end. If the needle were retracted, that natural bend would apply force to the needle seal, and potentially deform the seal. Deformation of the needle seal could cause a leak during subsequent use, allowing fluid or debris into the lumen of the vapor delivery system. Furthermore, if the needle is retracted into the lumen, the shape of the needle could change with extended time.

Upon opening the device packaging, a user should remove the tray retainer. As the shipping pin is snapped into the tray retainer, it naturally removes itself from the device during removal of the tray retainer. This was designed specifically to eliminate user interaction with the shipping pin.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A prostate treatment device, comprising:
an introducer shaft:
a vapor generator configured to generate a condensable vapor;
a vapor delivery needle in communication with the vapor generator and movably disposed within the introducer shaft;
a magnet attached to the needle;
a solenoid actuator disposed around the magnet, wherein the solenoid actuator comprises a first winding and a second winding; and
a power supply configured to simultaneously supply a first current to the first winding and a second current to the second winding in order to move a distal tip of the vapor delivery needle between a retracted position inside the introducer shaft and an extended position at least partially outside of the introducer shaft, wherein the first current is in a first direction opposite to a second direction of the second current, wherein the first winding is configured to generate a first magnetic field when the first current is applied to the first winding, and wherein the second winding is configured to generate a second magnetic field when the second current is applied to the second winding.

2. The device of claim 1, wherein the first magnetic field shares a polarity with the magnet.

3. The device of claim 2 wherein the second magnetic field has a polarity opposite to the polarity of the magnet.

4. The device of claim 1, wherein the first magnetic field generates a first force on the magnet.

5. The device of claim 4, wherein the second magnetic field generates a second force on the magnet in a same direction as the first force.

6. The device of claim 5, wherein a magnitude of a combination of the first force and the second force is approximately twice a magnitude of the first force alone.

7. The device of claim 1, wherein the magnet is at least partly within both of the first winding and the second winding in a retracted position of the vapor delivery needle.

8. The device of claim 1, further comprising a sensor configured to provide a voltage output proportional to a magnetic field produced by the magnet.

9. A prostate treatment device, comprising:
an introducer shaft;
a vapor generator configured to generate a condensable vapor;
a vapor delivery needle in communication with the vapor generator and slidably disposed within the introducer shaft a magnet attached to the needle; and
an actuator configured to selectively simultaneously apply to the magnet a first, repelling, force in a first direction and a second, attracting force in the first direction in order to move a distal tip of the vapor delivery needle between a retracted position inside the introducer shaft and an extended position at least partially outside of the introducer shaft, wherein the actuator includes a second magnet configured to generate a first magnetic field having a first polarity and a third magnet configured to generate a second magnetic field having a second polarity, and wherein the first polarity is opposite to the second polarity.

10. The device of claim 9, wherein the first magnetic field produces the first force, and wherein the second magnetic field produces the second force.

11. The device of claim 9, wherein a magnitude of a combination of the first force and the second force is approximately twice a magnitude of the first force alone.

12. The device of claim 9, further comprising a sensor configured to provide a voltage output proportional to a magnetic field produced by the first magnet.

13. A prostate treatment device, comprising:
an introducer shaft;
a vapor generator configured to generate a condensable vapor;
a vapor delivery needle in communication with the vapor generator and slidably disposed within the introducer shaft;
a magnet attached to the needle;
a solenoid actuator disposed around the magnet, wherein the solenoid actuator comprises a first winding and a second winding; and
a power supply configured to supply at least one current to the solenoid actuator, wherein the supply of the at least one current simultaneously causes (a) the first winding to generate a first magnetic field having a first polarity, and (b) the second winding to generate a second magnetic field having a second polarity, wherein the first polarity is opposite to the second polarity, wherein the first magnetic field shares a polarity with the magnet, and wherein the second magnetic field has a polarity opposite to a polarity of the magnet.

14. The device of claim 13, wherein the first magnetic field generates a first force on the magnet, wherein the second magnetic field generates a second force on the magnet, and wherein the second force is in a same direction as the first force.

15. The device of claim 14, wherein a magnitude of a combination of the first force and the second force is approximately twice a magnitude of the first force alone.

16. The device of claim 13, wherein the magnet is at least partly within both of the first winding and the second winding in a retracted position of the vapor delivery needle.

17. The device of claim 13, further comprising a sensor configured to provide a voltage output proportional to a magnetic field produced by the first magnet.

\* \* \* \* \*